US00PP18717P2

(12) United States Plant Patent
Austin

(10) Patent No.: US PP18,717 P2
(45) Date of Patent: Apr. 8, 2008

(54) SHRUB ROSE PLANT NAMED 'AUSDECORUM'

(50) Latin Name: *Rosa hybrida*
Varietal Denomination: AUSdecorum

(75) Inventor: David C. H. Austin, Wolverhampton (GB)

(73) Assignee: David Austin Roses Ltd., Albrighton, Wolverhampton (GB)

( * ) Notice: Subject to any disclaimer, the term of this patent is extended or adjusted under 35 U.S.C. 154(b) by 0 days.

(21) Appl. No.: 11/635,215

(22) Filed: Dec. 6, 2006

(51) Int. Cl.
*A01H 5/00* (2006.01)

(52) U.S. Cl. ..... Plt./108
(58) Field of Classification Search ..... Plt./108
See application file for complete search history.

*Primary Examiner*—Kent Bell
*Assistant Examiner*—S. B. McCormick-Ewoldt
(74) *Attorney, Agent, or Firm*—Kauth, Pomeroy, Peck & Bailey LLP

(57) ABSTRACT

Shrub rose plant substantially as herein shown and described, characterized particularly by its deep, rich crimson, medium-sized rosette shaped blossoms; a pleasing fruity fragrance; and short, bushy, upright growth.

1 Drawing Sheet

Genus and species: *Rosa hybrida.*
Variety denomination: 'AUSdecorum'.

ORIGIN OF THE INVENTION

The present invention relates to a new and distinct variety of a shrub rose plant named 'AUSdecorum' which was originated by me by crossing an unnamed, unpatented seedling with an unnamed, unpatented seedling.

BACKGROUND OF THE INVENTION

The primary objective of this breeding was to produce a very free flowering healthy variety having deep red blooms and a strong fragrance.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Deep, rich crimson, medium-sized rosette shaped blossoms.
2. A pleasing fruity fragrance.
3. Short, bushy upright growth.

Asexual reproduction of this new variety by budding as performed at Albrighton, England, shows that the foregoing and all other characteristics and distinctions come true to form and are established and transmitted through succeeding propagations.

Comparison with Parents

The seed parent has smaller blooms of a lesser petalage than those of 'AUSdecorum' and broader, less upright growth. The pollen parent has larger blooms with a slighter perfume.

Comparison with Similar Variety

'AUSromeo' (U.S. Plant Pat. No. 13,993) has more petals per bloom than 'AUSdecorum' and makes a taller, less compact shrub. 'AUSdecorum' has rosette-shaped blooms with a fruity fragrance compared with the quartered blooms and Old Rose fragrance of 'AUSromeo'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling (Unpatented).
*Pollen parent.*—Unnamed Seedling (Unpatented).

FLOWER

Observations made from plants connecting at one year of age grown in a garden environment at Albrighton, England.

Blooming habit: Recurrent. The number of blooms per plant during the growing season is profuse — there are too many to count.

Bud:
*Size.*—About 4 cm long and 2.8 cm in diameter when the petals start to unfurl.
*Form.*—The bud form is pointed ovoid.
*Color.*—When sepals first divide, bud color is Red Group 59A. When half blown, the upper sides of the petals are Red-Purple Group 64B and the lower sides of the petals are Red-Purple Group 64B with flecks of Red-Purple Group 71A.

*Sepals.*—Color: Upper surface: Green Group 143A with Green Group 143C at base. Lower surface: Yellow-Green Group 144A with Yellow-Green Group 144C at base and a touch of Orange-Red Group N34C along the central ridge. Length: 3.4 cm. Width: 0.8 cm. Shape: Subulate. Surface texture: Upper Surface: Smooth. Lower surface: Smooth. There are three lightly appendaged sepals. There are two unappendaged sepals with glandular edges.

*Receptacle.*—Color: Yellow-Green Group 144A. Shape: Campanulate. Size: Medium, about 1.0 cm long×0.8 cm wide. Surface: Smooth.

*Peduncle.*—Length: Medium, averaging about 5 cm. Surface: Glandular. Color: Yellow-Green Group 144B. Strength: Strong.

Bloom:

*Size.*—Large. Average open diameter is about 10.2 cm.

*Borne.*—In irregular compound corymb clusters of about three to five blooms.

*Stems.*—Strength: Strong. Average length is about 30 cm with a diameter of about 0.5 cm.

*Form.*—When first open: Cupped. Permanence: All petals curl.

*Petalage.*—Number of petals under normal conditions: 65–70.

*Color.*—The upper sides of the petals are Red-Purple Group 61A. The reverse sides of the petals are Red-Purple Group 61B. The base of each petal is Yellow Group 8B upper side and Yellow Group 10A under side.

*Variegations.*—None.

*Discoloration.*—The general tonality at the end of the first day is Red-Purple Group 61A. At the end of the third day: Red-Purple Group 71A.

*Fragrance.*—Strong, fruity.

Petals:

*Texture.*—Smooth and slightly velvety.

*Size.*—Width: 4.0 cm. Length: 4.9 cm.

*Surface.*—Smooth.

*Shape.*—Obovate. Margin: Flat and entire with slight undulation. Apex Shape: Obtuse. Base Shape: Cuneate. Form: Inner petals are incurved, outer petals are incurved with a reflexing margin.

*Arrangement.*—Imbricated.

*Petaloids.*—Number: 6. Color: Anther: Yellow Group 11A. Filament: Red Group 48A. Petal: Red-Purple Group 61B. Length: Anther: 3 mm, Filament: 5 mm, Petal: 6 mm.

*Persistence.*—Petals drop off cleanly before drying.

*Lastingness.*—On the plant: Fair (about 4 days). As a cut flower: Fair (about 5 days).

Reproductive parts:

*Stamens.*—Number: 15. Length: 8 mm. Anthers: Length: 3 mm. Color: Yellow-Orange Group 17A. Arrangement: Regular around styles, mixed with petaloids. Filaments: Color: Red Group 48A. Length: 5 mm. Pollen: Color: Yellow-Orange Group 17A.

*Pistils.*—Number: 33. Length: 9 mm. Styles: Color: Green-Yellow Group 1C. Length: 8 mm. Stigmas: Color: Yellow Group 11A. Length: 1 mm.

*Hips.*—None observed.

PLANT

*Form.*—Shrub.

*Growth.*—Medium vigor.

*Age at maturity.*—Two years.

*Mature plant.*—Height: 1 m. Width: 0.6 m.

*Rootstock.*—'Dr. Huey' in the USA. *Rosa dumetorum* 'Laxa' for the observed plants in the U.K.

Foliage: Number of leaflets on normal mid-stem leaves: 5–7 (including terminal leaflet).

*Size.*—Medium. About 16.3 cm long×12.6 cm wide.

*Quantity.*—Normal. Average number leaves per flowering stem: 8.

*Color.*—New foliage: Upper side: Yellow-Green Group 146A with Greyed-Purple Group 183A concentrated around margin. Lower side: Yellow-Green Group 146A overlaid with Greyed-Purple Group 183D. Old foliage: Upper side: Green Group 137A. Lower side: Green Group 137C.

Leaflets:

*Size.*—About 6.9 cm long×4.4 cm wide.

*Shape.*—Pointed oval.

*Base shape.*—Rounded.

*Apex shape.*—Some acuminate, some acute.

*Texture.*—Leathery.

*Edge.*—Serrated.

*Serrations.*—Single, small.

*Petiole.*—Color: Yellow-Green Group 144B with a red tint caused by glands on the upper surface, not concentrated enough to determine RHS color code. Length: 4–5 cm. Width: 2 mm. Surface texture: Smooth, with glands on upper side.

*Petiole rachis.*—Color: Yellow-Green Group 144B. Underside: With prickles.

*Stipules.*—Length: 3 cm, serrated. Color: Yellow-Green Group 144B with Green Group 137C along margin.

*Auricle shape.*—Subulate. Length: 8–10 mm. Width: 1 mm at base, tapering to a fine point. Color: Green Group 137C.

*Disease resistance.*—Resistant to powdery and downy mildew, blackspot and rust in normal growing conditions.

*Pest resistance.*—Not tested.

*Vein color.*—Yellow-Green Group N144D.

*Venation pattern.*—Reticulate.

Wood:

*New wood.*—Color: Yellow-Green Group 144A with a light overlay of Greyed-Purple Group 184A on side exposed to the sun. Bark: Smooth.

*Old wood.*—Color: Green Group 138A. Bark: Smooth.

Stems:

*Mature stem.*—Length: 30 cm. Diameter: 5 mm.

*Internode distance.*—4 cm. The above measurements are all variable, depending upon the growing conditions in a season.

Prickles:

*Quantity.*—On main canes from base: Ordinary, 7 per 5 cm stem length. On laterals from main canes: Ordinary, 4 per 5 cm per stem length.

*Form.*—Concave curved inward.

*Length.*—5–6 mm.

*Color when young.*—Greyed-Red Group 178C.

*Color when mature.*—Greyed-Orange Group 176A with an occasional touch of Greyed-Yellow Group 161A.

Small prickles:

*Quantity.*—On main stalks: None. On laterals: Few. 20–30 in bottom third of stem, none on remainder of stem.

*Color.*—When young: Greyed-Red Group 178C. When mature: Greyed-Orange Group 176A.

Winter hardiness: Not tested.

I claim:

1. A new and distinct variety of shrub rose plant substantially as herein shown and described, characterized particularly by its deep, rich crimson, medium-sized rosette shaped blossoms; a pleasing fruity fragrance; and short, bushy, upright growth.

* * * * *

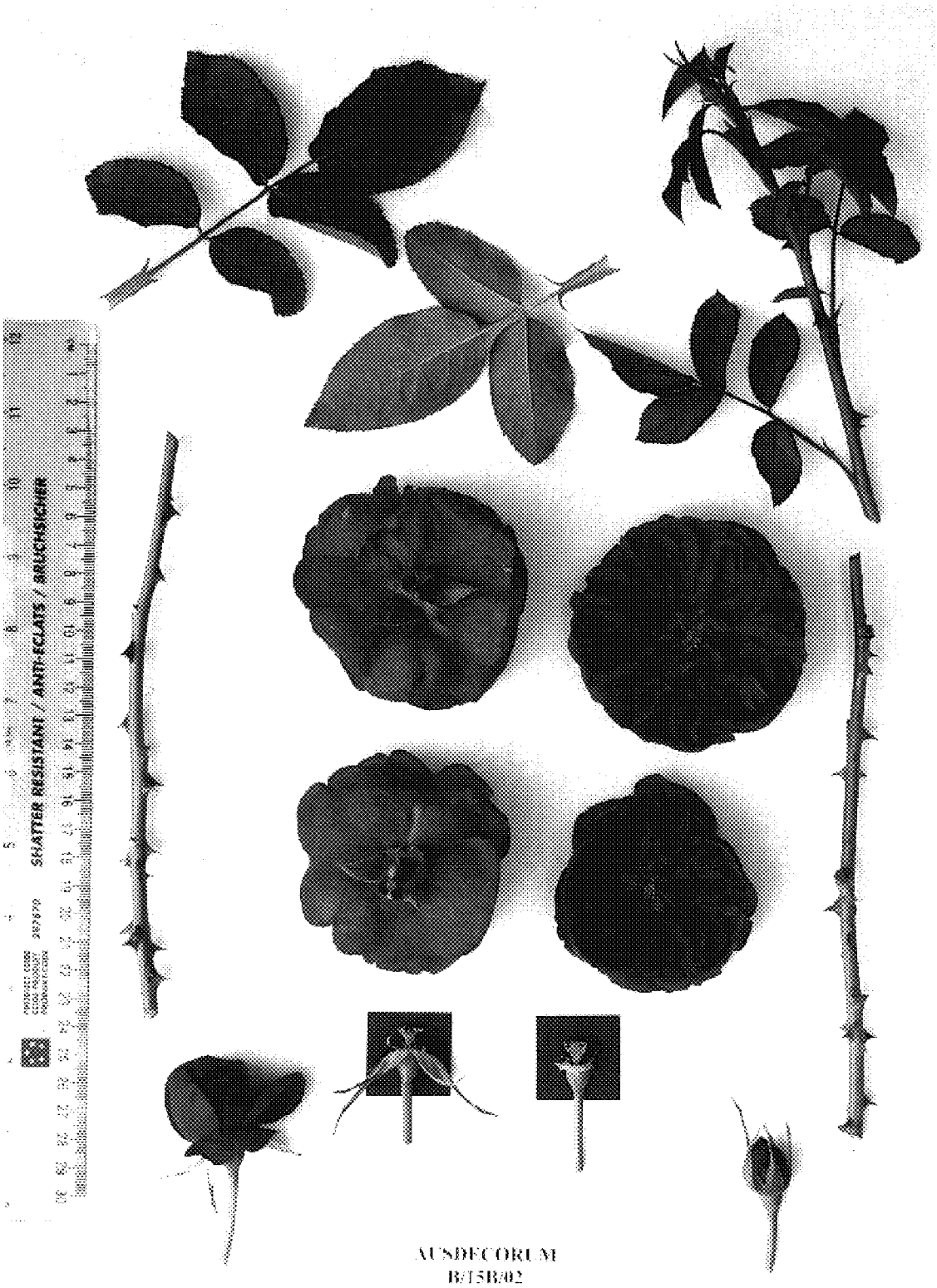
AUSDECORUM
B/T5B/02